United States Patent [19]

Senaratne

[11] Patent Number: 4,814,497

[45] Date of Patent: Mar. 21, 1989

[54] DEHALOGENATION PROCESS

[75] Inventor: K. Pushpananda A. Senaratne, Baton Rouge, La.

[73] Assignee: Ethyl Corporation, Richmond, Va.

[21] Appl. No.: 861,934

[22] Filed: May 12, 1986

[51] Int. Cl.⁴ .............................................. C07C 63/34
[52] U.S. Cl. ...................... 562/467; 560/56; 560/67; 560/103; 562/472; 562/475; 562/493
[58] Field of Search .............. 562/472, 475, 493, 467; 560/56, 67, 103

[56] References Cited

PUBLICATIONS

Mar., Advanced Organic Chemistry, Second Edition, McGraw-Hlll, N.Y. pp. 517-518.
Akagoh et al., Chemical Abstracts, vol. 103: 123081e 1985.

Primary Examiner—Werren B. Lone
Attorney, Agent, or Firm—Patricia J. Hogan

[57] ABSTRACT

Particulate aluminum is intimately mixed with an aromatic material that contains at least one ar-halo substituent having an atomic number above 20 and at least one side-chain halo substituent having an atomic number below 20 in the presence of an aqueous alkali or alkaline earth metal hydroxide so as to effect selective removal of the ar-halo substituent.

15 Claims, No Drawings

DEHALOGENATION PROCESS

FIELD OF INVENTION

This invention relates to a dehalogenation process and more particularly relates to the selective dehalogenation of aromatic materials having different ring and side-chain halo substituents.

BACKGROUND

As is well known, there are many useful aromatic compounds containing side chains which bear at least one halo substituent having an atomic number below 20. Such compounds may be synthesized by various techniques, including some otherwise attractive techniques which have the disadvantage of resulting in the formation of aromatic materials that contain unwanted ar-iodo or ar-bromo substituents as well as the desired halo-substituted side chains. Regardless of whether these ar-halo substituents are present in the same compound as the halo-substituted side chains or in a compound that is in admixture with the desired product, it is difficult to remove them without also removing the halo substituents on the side chains.

March, *Advanced Organic Chemistry*, Second Edition, McGraw-Hill, New York, pp. 517–518, teaches the use of various metals and metal compounds in removing halogen from aromatic rings. Akagah et al., *Chemical Abstracts*, Vol. 103, 123081e, 1985, teach that haloarenes, such as chlorobenzene and p-fluorotoluene, can be reduced with a particular activated aluminum.

SUMMARY OF INVENTION

An object of this invention is to provide a novel, selective process for reductively removing ar-iodo or bromo substituents from an aromatic material in the presence of fluoro or chloro moieties on a side chain.

Another object is to provide such a process which uses an easily-available reducing agent and is conducted under mild conditions.

These and other objects are attained by intimately mixing particulate aluminum with an aromatic material that contains at least one ar-halo substituent having an atomic number above 20 and at least one side-chain halo substituent having an atomic number below 20 in the presence of an aqueous alkali or alkaline earth metal hydroxide so as to effect selective removal of the ar-halo substituent.

DETAILED DESCRIPTION

Aromatic materials that can be selectively dehalogenated by the process of the invention are aromatic compounds and mixtures of aromatic compounds that contain at least one ar-halo substituent having an atomic number above 20 and at least one sidechain halo substituent having an atomic number below 20. Any such materials can be utilized, regardless of whether the aromatic rings in the materials are benzene, naphthalene, or other aromatic rings and regardless of whether the halo-substituted side chains are haloalkyl or haloalkenyl groups—the materials that are preferred naturally depending on the particular products that are desired. However, the materials most likely to be used as starting materials are apt to be materials wherein aliphatic chains in the compounds contain about 1–20 carbons, especially ar-haloaralkyl halides wherein the aromatic rings are benzene or naphthalene rings, mixtures of ar-halobenzene compounds with ar-(haloalkyl) benzene compounds, and mixtures of ar-halonaphthalene compounds with ar-(haloalkyl)naphthalene compounds.

In a particularly useful embodiment of the invention, the aromatic material is a mixture comprising at least two compounds corresponding to the formula:

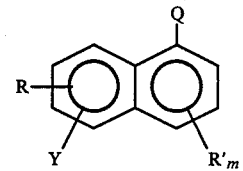

wherein:

R and R' are independently selected from chloro, fluoro, hydroxy, and alkyl and alkoxy substituents containing 1–6 carbons (e.g., methyl, ethyl, propyl, 1-methylethyl, butyl, 2-methylpropyl, 1,1-dimethylethyl, pentyl, hexyl, etc.);

Q is $-CN$, $-COOL$, or $-CTN(R'')CH_2COOL$;

L is hydrogen, alkali metal, or saturated hydrocarbyl (i.e., a hydrocarbyl group that is free of aliphatic unsaturation, such as methyl, ethyl, propyl, cyclohexyl, phenyl, tolyl, benzyl, or other alkyl, cycloalkyl, aryl, alkaryl, or aralkyl group, generally a group containing 1–10 carbons);

T is oxygen or sulfur;

R'' is an alkyl group containing 1–6 carbons (e.g., the alkyl groups exemplified above);

Y represents bromo or iodo in at least one of the compounds and, in at least one other compound of the mixture, represents $-(CF_2)_nCF_3$;

m is 0 or 1; and n is 0–20.

These are mixtures which are apt to be formed in the course of preparing the products of U.S. Pat. 4,439,617 (Sestanj et al.) and copending applications Ser. No. 724,474, filed Apr. 18, 1985 (Ramachandran et al.) and Ser. No. 808,000, filed Dec. 12, 1985 (Brandt), the teachings of all of which are incorporated herein by reference. Of these mixtures, those most apt to be encountered are mixtures of ar-bromo- or ar-iodonaphthalene compounds and ar-(trifluoromethyl)naphthalene compounds, especially those wherein Y is in the 5-position, R is an alkoxy group in the 6-position, and m is 0. Exemplary of such mixtures are methyl 5-bromo-6-methoxy-1-naphthoate/methyl 5-trifluoromethyl-6-methoxy-1-naphthoate, 5-bromo-6-methoxy-1-cyanonaphthalene/5-trifluoromethyl-6-methoxy-1-cyanonaphthalene, 5-bromo-6-methoxy-1-naphthoic acid/5-trifluoromethyl-6-methoxy-1-naphthoic acid, 5-bromo-6-methoxy-1-naphthoyl chloride/5-trifluoromethyl-6-methoxy-1-naphthoyl chloride, methyl N-[(5-bromo-6-methoxynaphthalenyl)carbonyl]-N-methylaminoethanoate/methyl N-[(5-trifluoromethyl-6-methoxynaphthalenyl)carbonyl]-N-methylaminoethanoate, methyl N-[(5-bromo-6-methoxynaphthalenyl)thiono]-N-methylaminoethanoate/methyl N-[(5-trifluoromethyl-6-methoxynaphthalenyl)thiono]-N-methylaminoethanoate, N-[(5-bromo-6-methoxynaphthalenyl)thiono]-N-methylaminoethanoic acid/N-[(5-trifluoromethyl-6-methoxynaphthalenyl)thiono]-N-methylaminoethanoic acid, the corresponding mixtures wherein the ar-halo substituent is iodo, the corresponding mixtures wherein the alkoxy group is another alkoxy group containing 1-6 carbons, the corresponding mixtures wherein the esterifying group is another saturated hydrocarbyl group, the corresponding mixtures wherein the trifluoromethyl group is replaced with a higher perfluoroalkyl group, the corresponding mixtures containing a higher perfluoroalkyl-substituted compound as an additional component, etc.

In addition to mixtures of the type exemplified above, other mixtures of compounds corresponding to the aforementioned formula, e.g., compounds wherein the substituents are in different positions and/or are replaced with other substituents covered by the formula, can also be treated by the process of the invention. Additionally, as indicated above, the invention can be used in the treatment of other aromatic compounds and mixtures having an undesired ar-bromo or ar-iodo substituent, e.g., o- or m-iodobenzotrifluoride, o-iodotoluene/o-(trifluoromethyl)toluene, 1,2-diiodobenzene/1,2-bis(trifluoromethyl)benzene, iodobenzne/benzotrifluoride, 4-iodostyrene/$\beta$-(trifluoromethyl)styrene, p-iodobenzoic acid/p-(undecafluoropentyl)benzoic acid, iodobenzene/(pentadecafluoroheptyl)benzene, 1-bromo-2-methylnaphthalene/1-pentadecafluoroheptyl-2-methylnaphthalene, the corresponding compounds and mixtures wherein the ar-halo substituent is bromo instead of iodo and/or the side-chain halo substituent is chloro instead of fluoro, etc.

In the practice of the invention, the aromatic material is intimately mixed with particulate aluminum in the presence of an aqueous alkali or alkaline earth metal hydroxide. The aluminum may be in the form of powder or granules and is preferably used in an amount such as to provide at least one equivalent, generally about 1-5 equivalents, of aluminum per equivalent of ar-halo substituent to be removed. The use of a smaller amount of aluminum would decrease the amount of ar-halo substituent that could be removed, and the use of a larger amount—although not harmful—would be uneconomical.

The hydroxide employed may be any alkali or alkaline earth metal hydroxide, i.e., sodium, potassium, lithium, rubidium, cesium, calcium, magnesium, barium, or strontium hydroxide, but is generally sodium or potassium hydroxide. The concentration of hydroxide theoretically required is only one equivalent per equivalent of ar-halo substituent to be removed. However, in actual practice it is found desirable to employ an excess of the hydroxide, e.g., at least about 1.5 equivalents, frequently about 3-10 equivalents. More hydroxide can be used if desired, but there is generally no advantage to using an unnecessarily high excess.

The dehalogenation is usually conducted in a solvent to facilitate intimate admixture of the reactants, although it is sometimes found that the water employed in the reaction will dissolve the aromatic material sufficiently to obviate the need for an additional solvent. When an additional solvent is employed, it may be any solvent suitable for the dissolution of the particular aromatic material being dehalogenated, and the solvent/water ratio in the reaction mixture may be varied to account for the degree of solubility of the aromatic material. In the case of the ar-bromoor ar-iodonaphthalene compound/ar-(trifluoromethyl)naphthalene compound mixtures mentioned above, the preferred solvents are generally alcohols, such as methanol, ethanol, isopropanol, etc.; and a desirable solvent/water volume ratio is apt to be about 1/1.

The dehalogenation may be conducted at any suitable temperature, room temperature being satisfactory, but higher temperatures, e.g., temperatures up to about 100° C., generally being preferred to speed the reaction. In the interest of accomplishing the selective dehalogenation in an optimum time without degrading the product, itis frequently preferred to conduct the reaction at temperature of about 70°-90° C.

The invention is advantageous as a means of removing undesired ar-bromo and ar-iodo substituents from aromatic materials which also contain side chains that bear desired chloro or fluoro substituents. It is particularly advantageous because of its use of a readily-available reducing agent and its use of mild conditions.

The following examples are given to illustrate the invention and are not intended as a limitation thereof.

EXAMPLE I

A suitable reaction vessel was charged with a solution in 5 ml of 10% sodium hydroxide and 4 ml of methanol of one gram of a crude 6-methoxy-5-trifluoromethyl-1-naphthoic acid (MTNA) containing 97.13 area percent of MTNA and 0.3 area percent of 6-methoxy-5-bromo-1-naphthoic acid (MBNA) by HPLC analysis, the remainder being other impurities. To the solution was added 0.1 g of aluminum granules, and the reaction mixture was then stirred overnight at room temperature and filtered, after which the filtrate was diluted with 20 ml of water and acidified with 15% HCl. The precipitated solid was filtered, dried, and subjected to HPLC analysis, which showed the product to contain 97.94 area percent of MTNA and no detectable amount of MBNA.

EXAMPLE II

A suitable reaction vessel was charged with a solution in 12.5 ml of 10% sodium hydroxide and 10 ml of methanol of 2.5 g of the crude MTNA of Example I. To the solution was added 0.25 g of aluminum granules, and the reaction mixture was then heated with stirring for four hours at 60°-68° C., cooled, and worked up as in Example I. GC/MS analysis showed the MBNA to be totally removed without any removal of fluorine from the side-chains.

COMPARATIVE EXAMPLE

Example I was essentially repeated except that the reduction was conducted at 115° C. Analysis of the product showed that about 20% of the side-chain fluorine had been removed.

It is obvious that many variations can be made in the products and processes set forth above without departing from the spirit and scope of this invention.

What is claimed is:

1. A selective dehalogenation process which comprises intimately mixing particulate aluminum with an aromatic material that contains at least one ar-halo substituent selected from bromo and iodo and at least one side chain containing a halo substituent selected from chloro and fluoro in the presence of an aqueous alkali or alkaline earth metal hydroxide so as to effect selective removal of the ar-halo substituent, said aromatic material being selected from ar-ahloaralkyl halides wherein the aromatic rings are benzene or naphthalene rings, mixtures of ar-halobenzene compounds with ar-(haloalkyl)benzene compounds, and mixtures of ar-halonaphthalene compounds with ar-(haloalkyl)naphthalene compounds.

2. The process of claim 1 wherein the aromatic material is an ar-haloaralkyl halide.

3. The process of claim 1 wherein the aromatic material is a mixture of an aromatic compound bearing at least one ar-halo substituent and a different aromatic compound bearing at least one haloalkyl substituent.

4. The process of claim 3 wherein the aromatic material is a mixture comprising at least two compounds corresponding to the formula:

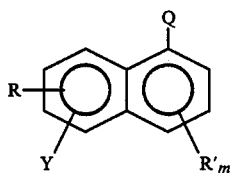

wherein R and R' are independently selected from chloro, fluoro, hydroxy, and alkyl and alkoxy substituents containing 1-6 carbons; Q is —CN, —COOL, or —CTN(R'')CH$_2$COOL; L is hydrogen, alkali metal, or saturated hydrocarbyl; T is oxygen or sulfur; R'' is an alkyl group containing 1-6 carbons; Y represents bromo or iodo in at least one of the compounds and, in at least one other compound of the mixture, represents —(CF$_2$)$_n$CF$_3$; m is 0 or 1; and n is 0-20.

5. The process of claim 4 wherein the aromatic material is a mixture of an ar-bromonaphthalene compound and an ar-(trifluoromethyl)naphthalene compound.

6. The process of claim 5 wherein the aromatic material is a mixture of a 6-alkoxy-5-bromo-1-naphthoic acid and a 6-alkoxy-5-trifluoromethyl-1-naphthoic acid.

7. The process of claim 1 wherein the hydroxide is an alkali metal hydroxide.

8. The process of claim 7 wherein the hydroxide is sodium hydroxide.

9. The process of claim 1 wherein the selective dehalogenation is conducted in a medium comprising water and an organic solvent.

10. The process of claim 9 wherein the organic solvent is an alcohol.

11. The process of claim 1 wherein the aluminum/ar-halo substituent equivalent ratio in the reaction mixture is at least about 1/1.

12. The process of claim 1 wherein the hydroxide/ar-halo substituent equivalent ratio in the reaction mixture is at least about 1.5/1.

13. The process of claim 1 wherein the hydroxide/ar-halo substituent equivalent ratio in the reaction mixture is at least about 3/1.

14. A selective dehalogenation process which comprises intimately mixing at least one equivalent of particulate aluminum with an aromatic material containing one equivalent of an ar-halo substituent having an atomic number above 20 in the presence of at least 1.5 equivalents of an aqueous alcoholic alkali or alkaline earth metal hydroxide so as to effect selective removal of the ar-halo substituent, the aromatic material being a mixture comprising at least two compounds corresponding to the formula:

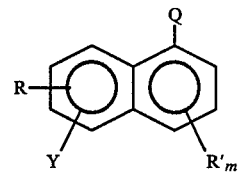

wherein R and R' are independently selected from chloro, fluoro, hydroxy, and alkyl and alkoxy substituents containing 1-6 carbons; Q is —CN, —COOL, or —CTN(R'')CH$_2$COOL; L is hydrogen, alkali metal or saturated hydrocarbyl; T is oxygen or sulfur; R'' is an alkyl group containing 1-6 carbons; Y represents bromo or iodo in at least one of the compounds and, in at least one other compound of the mixture, represents —(CF$_2$)$_n$CF$_3$; m is 0 or 1; and n is 0-20.

15. The process of claim 14 wherein the amount of hydroxide is at least about 3 equivalents.

* * * * *